United States Patent [19]
Pohl et al.

[11] Patent Number: 5,498,747
[45] Date of Patent: Mar. 12, 1996

[54] CARBODIIMIDES AND/OR OLIGOMERIC POLYCARBODIIMIDES BASED ON 1,3-BIS (1-METHYL-1-ISOCYANATOETHYL)BENZENE, THEIR PREPARATION, AND THEIR USE AS HYDROLYSIS STABILIZERS

[75] Inventors: Siegmund Pohl, Ludwigshafen; Friedhelm Lehrich, Lemfoerde; Manfred Genz, Damme; Bernd Bruchmann, Ludwigshafen; Helmut Tesch, Roedersheim-Gronau; Roland Minges, Gruenstadt; Joachim Streu, Dachau, all of Germany

[73] Assignee: BASF Aktiengesellschaft, Ludwigshafen, Germany

[21] Appl. No.: 400,406

[22] Filed: Mar. 7, 1995

Related U.S. Application Data

[62] Division of Ser. No. 241,912, May 12, 1994, abandoned.

[51] Int. Cl.$^6$ .................. C07C 269/02; C07C 273/10
[52] U.S. Cl. .................. 560/25; 524/195; 528/80; 528/83; 528/84; 560/27; 564/252
[58] Field of Search ............. 560/25, 27; 524/195; 528/80, 83, 84; 564/252, 56

[56] References Cited

U.S. PATENT DOCUMENTS

| | | | |
|---|---|---|---|
| 2,941,983 | 6/1960 | Smeltz | 260/77.5 |
| 3,193,522 | 7/1965 | Neumann et al. | 260/45.9 |
| 3,193,523 | 7/1965 | Neumann et al. | 260/45.9 |
| 4,419,294 | 12/1983 | Feldman et al. | 260/453 A |
| 5,008,363 | 4/1991 | Mallon et al. | 528/49 |
| 5,210,170 | 5/1993 | Quiring et al. | 528/80 |
| 5,246,993 | 9/1993 | Scherzer et al. | 524/195 |

FOREIGN PATENT DOCUMENTS

| | | |
|---|---|---|
| 460481A3 | 12/1991 | European Pat. Off. . |
| 113059 | 3/1898 | Germany . |
| 851936 | 10/1960 | United Kingdom . |

OTHER PUBLICATIONS

EPO Search Report dated Oct. 5, 1994; translation of EPO Search Report.

*Primary Examiner*—Peter O'Sullivan
*Attorney, Agent, or Firm*—Dennis V. Carmen

[57] ABSTRACT

The present invention relates to novel carbodiimides or oligomeric polycarbodiimides containing terminal isocyanate, urea and/or urethane groups, methods for their preparation, and their use as hydrolysis stabilizers.

4 Claims, No Drawings

CARBODIIMIDES AND/OR OLIGOMERIC POLYCARBODIIMIDES BASED ON 1,3-BIS (1-METHYL-1-ISOCYANATOETHYL)BENZENE, THEIR PREPARATION, AND THEIR USE AS HYDROLYSIS STABILIZERS

This is a continuation of application Ser. No. 08/241,912, filed May 12, 1994, abandoned.

The present invention relates to novel carbodiimides or oligomeric polycarbodiimides containing terminal isocyanate, urea and/or urethane groups, of the formula (I)

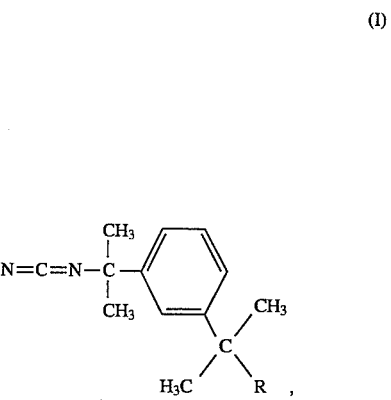

(I)

where the R radicals are identical or different and are selected from the group consisting of —NCO—, —NH-CONHR$^1$—, —NHCONR$^1$R$^2$— and —NHCOOR$^3$—, and n is an integer from 0 to 10, to a process for their preparation, and to their use as stabilizers against hydrolytic degradation of polyaddition and polycondensation products containing ester groups, preferably polyurethanes.

Organic carbodiimides are known. Their chemistry is described, for example, in Chemical Reviews, Vol. 53 (1953), pages 145 to 166, and Angewandte Chemie 74 (1962), pages 801 to 806.

Monocarbodiimides and oligomeric polycarbodiimides can be prepared, for example, by treating sterically hindered monoisocyanates or polyisocyanates with basic catalysts with elimination of carbon dioxide. Examples of suitable basic catalysts are, according to GB-A-1,083,410, heterocyclic compounds containing bonded phosphorus, and, according to DE-B-1 130 594 (GB-A-851,936), phospholenes and phospholidines, and oxides and sulfides thereof.

Furthermore, polycarbodiimides containing terminal urethane groups are described, for example, in U.S. Pat. No. 2,941,983, and DE-B-22 48 751 (U.S. Pat. No. 4,076,945). The products can be prepared, for example, by carbodiimidation of diisocyanates containing sterically hindered isocyanate groups and subsequent partial or full urethanization of the terminal NCO groups using alcohols. If aromatic diisocyanates containing isocyanate groups of differing reactivity are used, all or some of the isocyanate groups of relatively high reactivity can first be converted into the corresponding urethane groups using alcohol, and the remaining isocyanate groups can then be converted into carbodiimide groups with elimination of carbon dioxide. Oligomeric polycarbodiimides having a mean degree of condensation of from 2 to 30, which are obtainable by oligo condensation of 2,4'-diisocyanatodiphenylmethane or of a 3,3',5,5'-tetra-C$_1$— to —C$_4$-alkyl-4,4'-diisocyanatodiphenylmethane or of mixtures of these unsubstituted or alkyl-substituted diisocyanato-diphenylmethanes with further difunctional or polyfunctional aromatic isocyanates and, if desired, reacting all or some of the remaining free isocyanate groups of the resultant oligomeric polycarbodiimides with an aliphatic, araliphatic or cycloaliphatic alcohol or amine, are described in DE-A-41 26 359.

The carbodiimides are preferably used as stabilizers against hydrolytic cleavage of polyester-based plastics. According to DE-A-1 494 009 (U.S. Pat. No. 3,193,523), suitable compounds for this purpose are, in particular, 2- and 2'-substituted aromatic and/or cycloaliphatic monocarbodiimides, for example 2,2',6,6'-tetraisopropyldiphenlcarbodiimide. Polycarbodiimides having a molecular weight of greater than 500 and containing more than 3 carbodiimide groups are described in DE-B-1 285 747 (U.S. Pat. No. 3,193,522) as heat and moisture stabilizers in plastics containing ester groups. Although substantial stability of plastic containing ester groups against moist heat, water and water vapor can be achieved by adding these (poly)carbodiimides as stabilizers, the products also have disadvantages. The disadvantages of the tetra-alkyl-substituted monocarbodiimides which are preferred industrially, for example 2,2',6,6'-tetraisopopyldiphenylcarbodiimide, are their relatively high vapor pressure and, due to the low molecular weight, their tendency to migrate out of the polyaddition products, for example thermoplastic polyurethanes (TPUs), or polycondensation products, e.g. polyterephthalates. This deficiency can be overcome, according to EP-A-0 460 481 (CA-A-2, 043,820), by using substituted monocarbodiimides or oligomeric, substituted polycarbodiimides containing terminal isocyanate groups, which are prepared from substituted diisocyanates and which eliminate virtually no toxic, volatile substances originating from the carbodiimides used either at elevated temperature, for example under conventional processing conditions, or at room temperature. Polycarbodiimides of this type have relatively high melting points or are infusible and can only be introduced into the polyurethanes and/or their starting materials using complex equipment and at the expense of a considerable amount of time. Distribution of the polycarbodiimides in the plastics containing ester groups is therefore frequently insufficiently homogeneous, so that the stabilizer activity does not meet expectations. Conversion of some of the terminal isocyanate groups into urethane groups, for example in accordance with DE-A-22 48 751 or U.S. Pat. Nos. 2,941,983, allows lower-melting polycarbodiimide derivatives to be obtained.

It is an object of the present invention fully or at least partially to overcome the abovementioned disadvantages and to provide antihydrolysis agents which are homogeneously soluble in plastics containing ester groups, preferably polyurethanes and in particular TPU, without additional homogenization, steps being necessary. The antihydrolysis agents should have, in particular, a toxicologically improved behavior.

We have found that, surprisingly, this object is achieved by the use of 1,3-bis(1-methyl-1-isocyanatoethyl)benzene for the preparation of carbodiimides and/or oligomeric polycarbodiimides containing terminal isocyanate, urea and/or urethane groups.

The present invention accordingly provides carbodiimides and/or oligomeric polycarbodiimides of the formula (I)

groups, based on the molecular weight of the (poly)carbodiimides, their low vapor pressure, and the negligible migration and blooming behavior. The (poly)carbodiimides are highly compatible with the polyaddition and polycondensation products containing ester groups, in particular with polyester-urethane rubbers, and, due to their low melting point, are also readily homogeneously miscible with these materials in the melt.

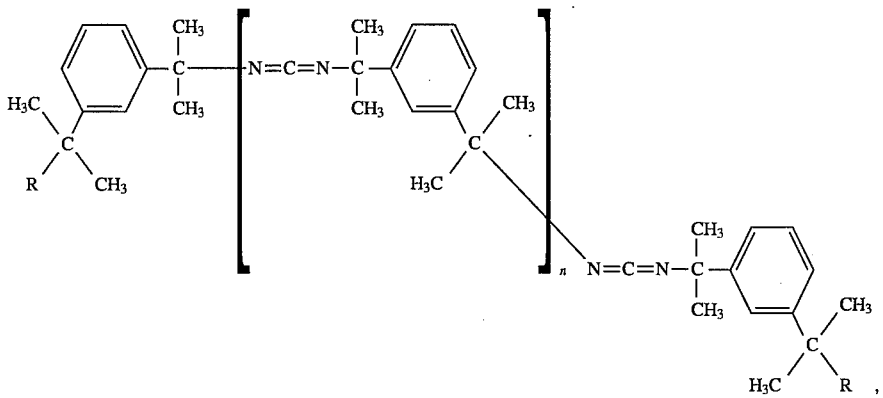

(I)

where
- the R radicals are identical or different and are selected from the group consisting of —NCO—, —NHCONHR$^1$—, —NHCONR$^1$R$^2$— and —NHCOOR$^3$—, where
  - R$^1$ and R$^2$ may be identical or different and are alkyl, cycloalkyl or aralkyl, and
  - R$^3$ is identical to R$^1$ or is alkoxypolyoxyalkylene, and
- n is an integer from 0 to 10.

The present invention furthermore provides processes for the preparation of the novel carbodiimides and/or oligomeric polycarbodiimides of the formulae (I) and (II) as defined in claims 1 and 2 and the use of the carbodiimides and/or oligomeric polycarbodiimides of the formulae (I) and (II) as stabilizers against hydrolytic degradation of polyaddition or polycondensation products containing bonded ester groups.

The novel carbodiimides and oligomeric polycarbodiimides contain sterically hindered isocyanate, urea and/or urethane groups bonded to a methylene group, exhibit an antihydrolysis action which is at least comparable to that of the aromatic carbodiimides and aromatic polycarbodiimides used in industry, but have increased light stability, and can be metered economically and easily without additional homogenization steps and introduced into the polycondensation and polyaddition products containing ester groups while observing occupational safety regulations. A further advantage is the large number of active carbodiimide Reaction of the novel carbodiimides and oligomeric polycarbodiimides with carboxylic acids and/or carboxyl-containing compounds gives araliphatic isocyanates of low reactivity compared with aromatic isocyanates. The araliphatic isocyanates formed therefore have virtually no effect on the characteristic number of the polyaddition reaction during urethane formation. Consequently, the molecular weights of the polyurethanes formed and therefore their mechanical properties are constant and highly reproducible. A further advantage is that the degradation products formed from the isocyanates contain no bonded aromatic amine groups and therefore can be regarded as relatively unproblematic from a toxicological point of view.

In addition to monomeric carbodiimides, oligomeric polycarbodiimides, advantageously those having a mean degree of condensation (number average) of from 2 to 10 preferably from 2 to 5, mixtures thereof or mixtures of monocarbodiimides and oligomeric polycarbodiimides can be used, since these can generally be introduced particularly readily into the polyaddition or polycondensation products containing ester groups to be stabilized. Polycarbodiimides with a high degree of condensation are generally solid compounds with a high melting point which are insufficiently compatible with the plastic matrix and therefore less readily homogeneously miscible with the polyaddition or polycondensation products.

The novel carbodiimides and oligomeric polycarbodiimides of the formula (II)

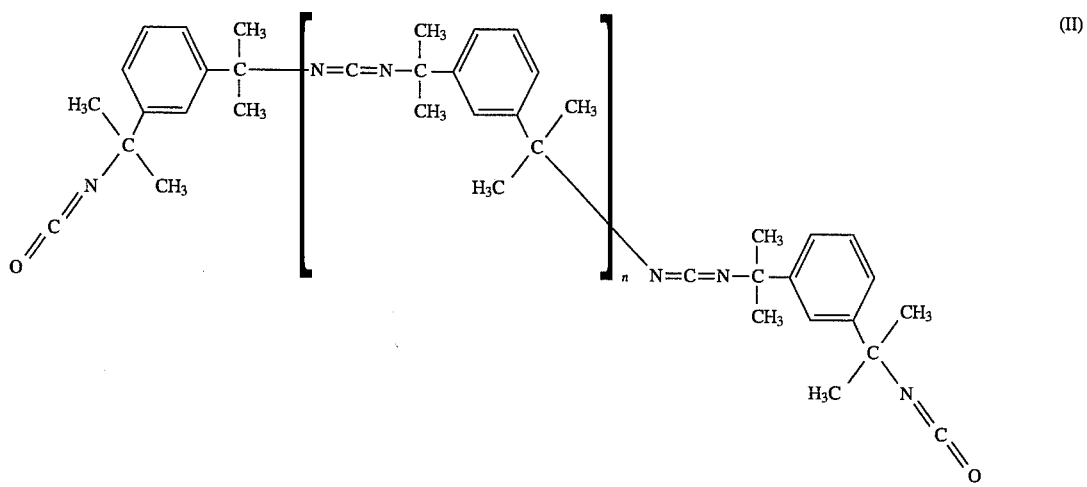

still contain reactive isocyanate groups and can therefore react with compounds containing NCO-reactive hydrogen atoms and in this way can be chemically bonded into the polyaddition or polycondensation products. In order to improve the shelf life of (poly)carbodiimides, all or some of the terminal isocyanate groups can be blocked, for example by means of C—H- or N—H-reactive compounds, e.g. ethyl malonate, acetylacetone, ethyl acetoacetate, phthalimide, caprolactam or benzene-sulfonamide, or partly or fully saturated by reaction with aliphatic, cycloaliphatic or araliphatic amines, alcohols or polyoxyalkylene alcohols, and their physical properties, for example their solubility or compatibility, can thus be modified in a targeted manner.

The isocyanate groups of the (poly)carbodiimides can be saturated, as stated above, using amines, alcohols and polyoxyalkylene alcohols. Suitable amines, for example primary or preferably secondary amines, advantageously have from 1 to 12 carbon atoms, preferably from 2 to 8 carbon atoms. Examples which may be mentioned are methylamine, ethylamine, propylamine, butylamine, pentylamine, hexylamine, 2-ethylhexylamine, octylamine, decylamine, diethylamine, dipropylamine, dibutylamine, methylbutylamine, ethylbutylamine, ethylhexylamine, cyclohexylamine and benzylamine. However, the isocyanate groups are preferably saturated using alcohols, for example primary or secondary alcohols having 1 to 18 carbon atoms, preferably 2 to 8 carbon atoms, and in particular alkoxy-polyoxyalkylene alcohols having 1 to 10 carbon atoms, preferably 1 to 4 carbon atoms, in the alkoxy group and having a molecular weight of from 76 to 2000, preferably 400 to 100 (number average). Examples which may be mentioned of primary or secondary alcohols are: methanol, ethanol, n-propanol, isopropanol, n-butanol, sec-butanol, n-pentanol, technical-grade pentanol mixtures, n-hexanol, technical-grade hexanol mixtures, 2-ethylhexanol, octanol, 2-ethyloctanol, decanol, dodecanol, cyclohexanol and benzyl alcohol. Examples of alkoxypolyoxyalkylene alcohols which have proven successful are polyoxybutylene alcohol, polyoxypropylene alcohol, polyoxypropylene-polyoxyethylene alcohol and preferably polyoxyethylene alcohol, which may contain, for example, a bonded methoxy, ethoxy, n- or isopropyoxy or n-butoxy group as terminal alkoxy group. Depending on the nature of the polyoxyalkylene radicals used, the (poly)carbodiimides can be rendered hydrophilic and water-soluble to hydrophobic and fat-soluble.

The novel carbodiimides and/or oligomeric polycarbodiimides can be prepared by condensing 1,3-bis(1-methyl(-1-isocyanatoethyl)benzene at elevated temperatures, for example at from 50° to 200° C., preferably at from 150° to 185° C., expediently in the presence of catalysts, with elimination of carbon dioxide. Processes which are suitable for this purpose are described, for example, in GB-A-1,083, 410, DE-B-1 130 594 (GB-A-851,936) and DE-A-11 56 401 (U.S. Pat. No. 3,502,722). Examples of catalysts which have proven highly suitable are phosphorus compounds, preferably selected from the group consisting of phospholenes, phospholene oxides, phospholidines and phospholidine oxides. The polycarbodiimide formation is usually terminated from the reaction mixture as the desired content of NCO groups, corresponding to a degree of condensation n of up to 10. To this end, the catalysts can be removed by distillation under reduced pressure or deactivated by adding a deactivator, e.g. phosphorus trichloride. The polycarbodiimide preparation can furthermore be carried out in the presence or absence of solvents which are inert under reaction conditions.

A suitable choice of the reaction conditions, for example the reaction temperature, the type and amount of catalyst and the reaction time, allows the person skilled in the art to set the degree of condensation in the conventional manner. The course of the reaction can be monitored most simply by determining the NCO content. Other parameters, for example the increase in viscosity, the deepening of color or the evolution of $CO_2$, can also be employed for monitoring the reaction.

When the condensation is complete, the free terminal isocyanate groups of the carbodiimide and/or of the oligomeric polycarbodiimides can, as stated above, be blocked by means of C—H- or N—H-reactive hydrogen compounds or fully or partly saturated by means of aliphatic, cycloaliphatic and/or araliphatic amines, alcohols and/or alkoxypolyoxyalkylene alcohols. In an advantageous embodiment, the aliphatic, cycloaliphatic or araliphatic amines, alcohols and/or alkoxypolyoxyalkylene alcohols are preferably added to the (poly)carbodiimide-containing reaction mixture in a slight excess of —OH—, —NH and/or —$NH_2$ groups relative to NCO groups in order to fully saturate the isocyanate groups, and are then allowed to react to completion, and any unreacted amount is then preferably removed by distillation under reduced pressure.

In another, preferred variant, the novel (poly)carbodiimides containing partly or fully saturated isocyanate groups can be prepared by first reacting up to 50% by weight, preferably up to 23% by weight, of the isocyanate groups of 1,3-bis(1-methyl-1-isocyanatoethyl)benzene with at least one aliphatic, cycloaliphatic or araliphatic amine, alcohol and/or alkoxypolyoxyalkylene alcohol, and then condensing all or some of the free isocyanate groups in the presence of catalysts with elimination of carbon dioxide to give carbodiimides and/or oligomeric polycarbodiimides.

The novel monocarbodiimides and/or oligomeric polycarbodiimides are highly suitable as acceptors for carboxyl compounds and are therefore preferably used as stabilizers against hydrolytic degradation of polycondensation products containing bonded ester groups, e.g. polyesters, polyether esters, polyester amides and polycaprolactones, and polyaddition products such as polyurethanes, polyureas and polyurethane-polyurea elastomers. Due to the good solubility, in particular of the monocarbodiimides, in the formative components for the preparation of polyurethanes and the good compatibility, in particular of oligomeric polycarbodiimides, with the polyurethanes formed and the reactivity of the NCO-containing (poly)carbodiimides with compounds containing reactive hydrogen atoms, the novel (poly)carbodiimides are particularly suitable as stabilizers against hydrolytic degradation of polyurethanes, preferably compact or cellular polyurethane elastomers, and in particular TPU.

The concentration of the novel monocarbodiimides and/or oligomeric polycarbodiimides in the polycondensation or polyaddition products containing ester groups which are to be stabilized is generally from 0.05 to 10% by weight, preferably from 0.1 to 5% by weight. In individual cases, depending on the susceptibility of the plastic to hydrolysis, the concentration may be higher.

Various methods can be used to introduce the monocarbodiimides and/or oligomeric polycarbodiimides which can be used according to the invention into the polyaddition or polycondensation products containing ester groups which are to be stabilized. For example, the novel (poly)carbodiimides can be mixed with one of the formative components for the preparation of polyaddition products, e.g. the polyisocyanates and/or polyhydroxyl compounds for the preparation of polyurethanes, or metered into the reaction mixture for the preparation of polyurethanes. In another procedure, the novel (poly)carbodiimides can be incorporated into the melt of the fully reacted polyaddition or polycondensation products. However, it is also possible to coat granules of the polyaddition or polycondensation products with the novel (poly)carbodiimides and to introduce these granules into the plastic compositions during subsequent production of moldings by melt extrusion. In a preferred embodiment, cast polyurethane elastomers and TPU based on polyester-polyols are prepared by first treating the carboxyl-containing polyester-polyols with the novel (poly)carbodiimides in order to reduce the acid content and then reacting them, with or without addition of further amounts of (poly)carbodiimides, with polyisocyanates, in the presence or absence of addition auxiliaries and additives.

In addition to effectiveness as stabilizers against hydrolytic degradation of polyaddition or polycondensation products containing ester groups or for the acidification of polyester-ols, which can be used for the preparation of polyester-containing plastics, in particular polyurethane rubbers, the monocarbodiimides and/or oligomeric polycarbodiimides are also suitable, for example, for the termination of esterification reactions during the preparation of polyesters when the desired degree of polycondensation has been reached.

EXAMPLES

Example 1

750 parts by weight (3.1 mol) of 1,3-bis(1-methyl-1-isocyanatoethyl)benzene having an NCO content of 34.4% by weight were heated to 180° C. in the presence of 1.5 parts by weight of 1-methyl-2-phospholene 1-oxide in the absence of a solvent and condensed at this temperature with moderate evolution of carbon dioxide. When the reaction mixture had reached an NCO content of 5.2% by weight, requiring a reaction time of approximately 22 hours, the catalyst added and residues of unreacted 1,3-bis(1-methyl-1-isocyanatoethyl)benzene were removed by distillation at 190° C./0.2 mbar.

549 parts by weight of a mixture of monocarbodiimides and oligomeric polycarbodiimides having an NCO content of 4.5% by weight, a content of —N═C═N groups of 141 mg/g, a melting point of <30° C. and an iodine color index of 4.0, measured in accordance with DIN 6162, were obtained.

The structure of the isocyanate group-containing mixture of monocarbodiimides and oligomeric polycarbodiimides was elucidated by means of the $^1$H-NMR and IR spectra.

Example 2

750 parts by weight (3.1 mol) of 1,3-bis(1-methyl-1-isocyanatoethyl)benzene having an NCO content of 34.4% by weight were heated to 180° C. in the presence of 1.5 parts by weight of 1-methyl-2-phospholene 1-oxide in the absence of a solvent and condensed at this temperature with evolution of carbon dioxide. When an NCO content of 5% by weight had been reached, requiring a reaction time of approximately 2 hours, 495 parts by weight of a methoxypolyoxyethylene alcohol having a mean molecular weight (number average) of 520 g/mol were added with stirring. The terminal NCO groups were converted into urethane groups over a period of 30 minutes while the reaction temperature of 180° C. was maintained.

The 1-methyl-2-phospholene 1-oxide added as catalyst and residues of unreacted 1,3-bis(1-methyl-1-isocyanatoethyl)benzene were then removed by distillation at 190° C./0.5 mbar.

1049 parts by weight of an NCO group-free mixture of monocarbodiimides and oligomeric polycarbodiimides containing terminal methoxypolyoxyethylene-urethane groups and having a content of —N═C═N groups of 76 mg/g, a viscosity, measured at 25° C. by the Ubbelohde method, of 15,620 mPa·s and an iodine color index, measured after dilution with monochlorobenzene in a volume ratio of 1:5, of 3.8, were obtained. The mixture was only sparingly soluble in water.

The structure of the urethane group-containing mixture of monocarbodiimides and oligomeric polycarbodiimides was elucidated by means of the $^1$H-NMR and IR spectra.

Example 3

The procedure was similar to that described in Example 2, but the 1,3-bis(1-methyl-1-isocyanatoethyl)benzene was condensed to an NCO content of 9.3% by weight.

The NCO group-containing mixture of monocarbodiimides and oligomeric polycarbodiimides was then urethanized by reaction with 957 parts by weight of a methoxypolyoxyethylene alcohol having a mean molecular weight of 520 (number average) by a method similar to that described in Example 2, and distilled.

1576 parts by weight of an NCO group-free mixture of monocarbodiimides and oligomeric polycarbodiimides containing terminal methoxypolyoxyethylene-urethane groups which had a content of —N═C═N groups of 50 mg/g, a viscosity, measured at 25° C. by the Ubbelohde method, of 1950 mPa·s and an iodine color index, measured after dilution with monochlorobenzene in a volume ratio of 1:5, of 2.4, were obtained. The mixture was highly soluble in water at 23° C.

The structure of the urethane group-containing mixture of monocarbodiimides and oligomeric polycarbodiimides was elucidated by means of the $^1$H-NMR and IR spectra.

Immediately after their production and after storage in water at 80° C. for 21 days, the test specimens were analyzed for tensile strength in accordance with DIN 53 504 and elongation at break in accordance with DIN 53 504.

The carbodiimides and/or oligomeric polycarbodiimides used, their amounts and the mechanical properties measured are summarized in the Table.

TABLE

| | Carbodiimide and/or oligomeric polycarbodiimide prepared | | Tensile strength after | | Elongation at break after | |
|---|---|---|---|---|---|---|
| | Type | Amount [% by weight, based on TPU] | 0 [MPa] | 21 days [MPa] | 0 [%] | 21 days [%] |
| Comparative Example | | | | | | |
| I | — | — | 51 | 2 | 590 | 75 |
| II | from 2,6-diisopropylphenyl isocyanate | 0.65 | 59 | 37 | 620 | 680 |
| III | from triisopropylphenyl isocyanate | 0.65 | 54 | 40 | 610 | 700 |
| Example | | | | | | |
| 5 | according to Example 1 | 0.65 | 60 | 39 | 630 | 780 |
| 6 | according to Example 1 | 1.00 | 60 | 38 | 670 | 750 |
| 7 | according to Example 1 | 1.30 | 57 | 35 | 670 | 750 |
| 8 | according to Example 2 | 0.65 | 52 | 36 | 580 | 520 |
| 9 | according to Example 4 | 0.65 | 56 | 37 | 560 | 530 |

Example 4

The procedure was similar to that described in Example 2, but the 1,3-bis(1-methyl-1-isocyanatoethyl)benzene was condensed to an NCO content of 7.9% by weight.

The NCO group-containing mixture of monocarbodiimides and oligomeric polycarbodiimides was then urethanized by means of 183 parts by weight of 2-ethyl-1-hexanol by a method similar to that described in Example 2 in order to react some of the NCO groups, and was distilled.

The resultant mixture of 843 parts by weight of monocarbodiimides and oligomeric polycarbodiimides containing terminal 2-ethylhexyl-urethane groups still had an NCO content of 1.8% and had a content of —N=C=N groups of 94 mg/g, a melting point of <30° C. and an iodine color index, measured after dilution with monochlorobenzene in a volume ratio of 1:5, of 1.5.

The structure of the urethane group-containing mixture of monocarbodiimides and oligomeric polycarbodiimides was elucidated by means of the $^1$H-NMR and IR spectra.

Preparation of thermoplastic polyurethanes stabilized by means of the novel mixture of monocarbodiimides and oligomeric polycarbodiimides Thermoplastic polyurethane granules prepared by reacting 440 g (1.76 mol) of 4,4'-diphenylurethane diisocyanate, 1000 g (0.5 mol) of 1,4-butanediol, 1,6-hexanediol polyadipate and 113 g (1.26 mol) of 1,4-butanediol, and, as hydrolysis stabilizer, carbodiimides and/or oligomeric polycarbodiimides were used to produce test specimens by injections molding.

We claim:

1. A process for the preparation of a carbodiimide or oligomeric polycarbodiimide of the formula;

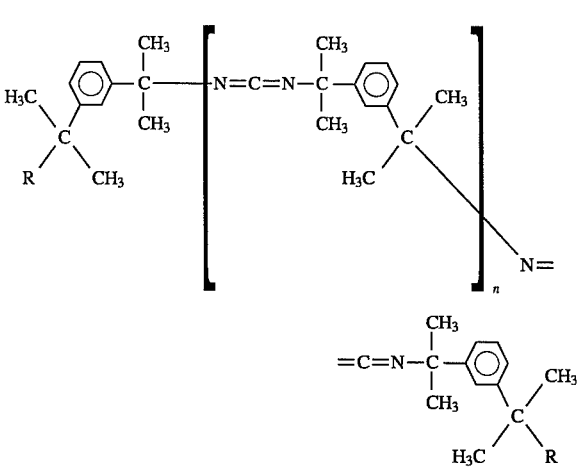

where the R radicals are identical or different and are selected from the group consisting of —NCONHR$^1$, —NHCONR$^1$R$^2$—, and —NHCOOR$^3$—, where R$^1$ and R$^2$ may be identical or different and are alkyl, cycloalkyl, or aralkyl, and R$^3$ is identical to R$^1$ or is alkoxypolyoxyalkylene, and n is an integer from 0 to 10, which comprises a) condensing 1,3-bis(1-methylisocyanatoethyl)benzene in the presence of catalysts with elimination of carbon dioxide, subsequently reacting all or some of the free terminal isocyanate groups of the resultant (poly)carbodiimide with at least one aliphatic, cycloaliphatic or araliphatic amine, alcohol and/or alkoxypolyoxyalkylene alcohol, and then removing or deactivating the catalysts, or b) reacting up to 50% of the isocyanate groups of 1,3-bis(1-methyl-1-isocyanatoethyl)benzene with at least one aliphatic, cycloaliphatic or araliphatic amine, alcohol and/or alkoxypolyoxyalkylene alcohol, subsequently condensing all or some of the free isocyanate groups in the presence of catalyst with elimination of carbon dioxide, and then removing or deactivating the catalysts.

2. The process of claim 1, which comprises condensing 1,3-bis(1-methyl-1-isocyanatoethyl)-benzene in the presence of catalyst with elimination of carbon dioxide, subsequently reacting all or some of the free terminal isocyanate groups of the resultant (poly)carbodiimide with at least one aliphatic, cycloaliphatic or araliphatic amine, alcohol and/or alkoxypolyoxyalkylene alcohol, and then removing or deactivating the catalysts.

3. The process as claimed in claim 1, wherein the catalyst used for the condensation is at least one phosphorus compound selected from the group consisting of phospholenes, phospholene oxides, phospholidines and phospholidine oxides.

4. The process as claimed in claim 2, wherein the catalyst used for the condensation is at least one phosphorus compound selected from the group consisting of phospholenes, phospholene oxides, phospholidines and phospholidine oxides.

* * * * *